(12) United States Patent
Higuchi et al.

(10) Patent No.: US 10,336,986 B2
(45) Date of Patent: Jul. 2, 2019

(54) CELL CULTURING ARTICLE AND METHOD FOR MANUFACTURING THEREOF

(71) Applicant: National Central University, Taoyuan (TW)

(72) Inventors: Akon Higuchi, Taoyuan (TW); Ta-Chun Kao, Taipei (TW)

(73) Assignee: National Central University, Taoyuan (TW)

( * ) Notice: Subject to any disclaimer, the term of this patent is extended or adjusted under 35 U.S.C. 154(b) by 17 days.

(21) Appl. No.: 15/893,716

(22) Filed: Feb. 12, 2018

(65) Prior Publication Data

US 2018/0230437 A1    Aug. 16, 2018

Related U.S. Application Data

(62) Division of application No. 14/188,704, filed on Feb. 25, 2014, now Pat. No. 9,902,941.

(30) Foreign Application Priority Data

Oct. 2, 2013  (TW) .............................. 102135687 A (51) Int. Cl.
| C12M 1/12 | (2006.01) |
| C12N 5/00 | (2006.01) |
| C12N 5/071 | (2010.01) |
| C12N 5/074 | (2010.01) |
| C12N 5/0735 | (2010.01) |

(52) U.S. Cl.
CPC ........... *C12N 5/0696* (2013.01); *C12M 25/00* (2013.01); *C12N 5/0062* (2013.01); *C12N 5/0606* (2013.01); *C12N 5/0628* (2013.01); *C12N 2533/30* (2013.01); *C12N 2533/52* (2013.01)

(58) Field of Classification Search
None
See application file for complete search history.

(56) References Cited

U.S. PATENT DOCUMENTS

| 5,108,428 | A | 4/1992 | Capecchi et al. |
| 5,897,955 | A | 4/1999 | Drumheller |
| 8,168,433 | B2 | 5/2012 | Gehman et al. |
| 8,329,469 | B2 | 12/2012 | Fadeev et al. |
| 9,902,941 | B2 * | 2/2018 | Higuchi .............. C12N 5/0062 |
| 2004/0063206 | A1 | 4/2004 | Rowley et al. |
| 2004/0209360 | A1 | 10/2004 | Keith et al. |
| 2009/0191627 | A1 | 7/2009 | Fadeev et al. |
| 2009/0191634 | A1 | 7/2009 | Martin et al. |
| 2010/0248366 | A1 | 9/2010 | Fadeev et al. |

FOREIGN PATENT DOCUMENTS

| CN | 102137924 A | 7/2011 |
| EP | 2420564 A2 | 2/2012 |
| JP | 03-148063 A | 6/1991 |
| JP | 2004-279204 A | 10/2004 |
| JP | 2009-050171 A | 3/2009 |
| JP | 2011-010581 A | 1/2011 |
| JP | 2011510655 | 4/2011 |
| JP | 2011-254719 A | 12/2011 |
| WO | 2011014605 A1 | 2/2011 |
| WO | 2012133900 A1 | 10/2012 |

OTHER PUBLICATIONS

Kobayashi et al. (Biomaterials 1991), vol. 12 October, 747-751.
Schmedlen et al. J Biomaterials 23 (2002), 4325-4332.
Higuchi A, Ling QD, Hsu ST, Umezawa A,"Biomimetic Cell Culture Proteins as Extracellular Matrices for Stem Cell Differentiation",Chemical Reviews,2012,vol. 112, p. 4507-4518, p. 4527-4528.
Eduard Rodriguez Perez, et al. "Polymer chains incorporating caprolactone and arginine-glycine-aspartic acid functionalities: Synthesis, characterization and biological response in vitro of the Schwann cell",Journal of Bioactive and Compatible Polymers,2012,vol. 28, p. 50-59.
Christie M. Hassan, Nikolaos A. Peppas,"Structure and Applications of Poly(vinyl alcohol) Hydrogels Produced by Conventional Crosslinking or by Freezing/Thawing Methods",Advances in Polymer Science,2000,vol. 153, p. 37-39, p. 57-59.
Melkoumian, Z. et al. "Synthetic peptide-acrylate surfaces for long-term self-renewal and cardiomyocyte differentiation of human embryonic stem cells.", Nature biotechnology 28, 606-610 (2010).

(Continued)

*Primary Examiner* — Blaine Lankford
(74) *Attorney, Agent, or Firm* — CKC & Partners Co., LLC (57) ABSTRACT

The disclosure provides a cell culturing article. The cell culturing article includes a substrate having a surface, a hydrophilic copolymer layer positioned on the surface of the substrate, and a plurality of peptide chains individually conjugated to a surface of the hydrophilic copolymer layer. The hydrophilic copolymer layer is copolymerized by a plurality of polyvinyl alcohol units, a plurality of polyvinyl alcohol derivative units, and a plurality of units containing at least one carboxyl group. A method for manufacturing the cell culturing article, a method for culturing undifferentiated stem cells and a method for regulating stem cell differentiation are also provided herein.

9 Claims, 7 Drawing Sheets

(56) References Cited

OTHER PUBLICATIONS

Kumar, S et al., "The combined influence of substrate elasticity and surface-grafted molecules on the ex vivo expansion of hematopoietic stem and progenitor cells.", Biomaterials 34 (2013) 7632-7644.

Tomoharu Konno, "Design of Cytocompatible Biointerfaces Based on Phospholipid Polymers to Standardize Cells and to contribute to Cell Engineering", Japanese Journal of Polymer Science and Technology, 2012, vol. 69, No. 10, pp. 555-566.

Yuko Niizato et al., "Mouse embryonic stem cells culture on hydrogels and maintenance of their undifferentiated state", Polymer Preprints, Japan, 2009, vol. 58, No. 2, p. 4936.

* cited by examiner

Providing a cell culturing article, wherein the cell culturing article includes a substrate, a hydrophilic copolymer layer positioned on the substrate, and a plurality of peptide chains individually conjugated on the hydrophilic copolymer layer
510

Culturing a plurality of undifferentiated stem cells in the cell culturing article and in a cell culturing medium having definite chemical composition
520

Culturing the undifferentiated stem cells in the cell culturing medium having definite chemical composition continuously for at least five passages
530

CELL CULTURING ARTICLE AND METHOD FOR MANUFACTURING THEREOF

RELATED APPLICATIONS

The present application is a Divisional Application of the U.S. application Ser. No. 14/188,704, filed Feb. 25, 2014, which claims priority to Taiwan Application Serial Number 102135687, filed Oct. 2, 2013, all of which are herein incorporated by reference in their entireties.

BACKGROUND

Technical Field

The present disclosure relates to a cell culturing article, and more particularly to a cell culturing article containing a hydrophilic copolymer layer.

Description of Related Art

A general cell culturing article commonly has a substrate, a polymethacrylate layer and specific peptide chains. The polymethacrylate layer is positioned on the substrate, and the specific peptide chain is conjugated on the surface of the polymethacrylate layer.

The general cell culturing article is formed by the conjugation of receptors on the surface of a cell to be cultured with the specific peptide chains on the polymethacrylate layer, such that the cell can adhere onto the surface of the polymethacrylate layer, rather than liable to suspend in a cell culture medium, which otherwise will lead to death of cells being cultured. However, the polymethacrylate layer in nature has a poor hydrophilicity, so that cells are not liable to adhere onto the surface of the polymethacrylate layer, which leads suspension of cells in the cell culture medium, and even leads to death of cells.

Additionally, in a natural environment, since a certain range of elastic stress exists between an undifferentiated stem cell and a tissue, the elastic stress may induce the undifferentiated stem cell to be differentiated to a specific cell. However, the general cell culturing article can only induce the stem cell to be differentiated to a specific type of cell by additionally adding cell growth factors and cell differentiation factors. Although adding the cell growth factors and the cell differentiation factors may induce stem cell differentiation, it is not easy to regulate differentiation specificity of stem cells as well as facilitating proliferation of the specific cells at the same time.

Therefore, there is a need for an improved cell culturing article and a manufacturing method thereof, so as to solve the aforementioned problems met in the art.

SUMMARY

The present disclosure provides a cell culturing article and a manufacturing method thereof, to solve problems caused by a conventional cell culturing article and improve proliferation of stem cells and differentiated cells, thereby increasing the differentiation specificity of stem cells.

An embodiment of the present disclosure provides a cell culturing article. The cell culturing article includes a substrate, a hydrophilic copolymer layer and a plurality of peptide chains.

The substrate has a surface, and the hydrophilic copolymer layer is positioned on the surface of the substrate. The hydrophilic copolymer layer is copolymerized by a plurality of polyvinyl alcohol units, a plurality of polyvinyl alcohol derivative units, and a plurality of units containing at least one carboxyl group. The peptide chains are individually conjugated on a surface of the hydrophilic copolymer layer.

According to an embodiment of the present disclosure, the polyvinyl alcohol derivative units include polyvinyl acetate, polyvinyl methyl ether or polyvinyl ethyl ether.

According to an embodiment of the present disclosure, the units containing at least one carboxyl group include itaconic acid.

According to an embodiment of the present disclosure, in the hydrophilic copolymer layer, the content percentages of the polyvinyl alcohol unit, the polyvinyl alcohol derivative unit and the unit containing at least one carboxyl group are individually about 65-98.7%, 0-30% and 1.3-5%.

According to an embodiment of the present disclosure, in the hydrophilic copolymer layer, the content percentage of the polyvinyl alcohol unit, the polyvinyl alcohol derivative unit and the unit containing at least one carboxyl group are individually about 85%, 10% and 5%.

According to an embodiment of the present disclosure, the hydrophilic copolymer layer has an elastic coefficient. According to an embodiment of the present disclosure, the elastic coefficient is in a range of 1 kPa to 100 kPa.

According to an embodiment of the present disclosure, the peptide chains include an oligopeptide, a polypeptide, a protein or a combination thereof. According to an embodiment of the present disclosure, the oligopeptide includes a fragment CS-1 of fibronectin (FN) or a fragment of vitronectin (VN). According to an embodiment of the present disclosure, the protein includes the fibronectin (FN) or a fragment of vitronectin (VN).

According to an embodiment of the present disclosure, the amino acids of the peptide chain are individually conjugated to the unit containing at least one carboxyl group via amide bonds.

Another aspect of the present disclosure provides a manufacturing method of cell culturing article. This manufacturing method includes the following steps. A substrate having a surface is provided. A hydrophilic copolymer layer is formed on the substrate, wherein the hydrophilic copolymer layer is copolymerized by a plurality of polyvinyl alcohol units, a plurality of polyvinyl alcohol derivative units, and a plurality of units containing at least one carboxyl group, through a copolymerization reaction. A cross linking reaction is performed, such that the plurality of polyvinyl alcohol units of the hydrophilic copolymer layer are cross-linked with each other. The plurality of peptide chains are individually conjugated on a surface of the hydrophilic copolymer layer.

According to an embodiment of the present disclosure, the manufacturing method further includes preparing a hydrophilic copolymer solution, and coating the hydrophilic copolymer solution on the surface of the substrate to form a hydrophilic copolymer layer.

According to an embodiment of the present disclosure, the hydrophilic copolymer solution includes a hydrophilic copolymer, and the concentration of the hydrophilic copolymer is about 0.05-0.2 wt %.

According to an embodiment of the present disclosure, the polyvinyl alcohol derivative units include polyvinyl acetate, polyvinyl methyl ether or polyvinyl ethyl ether.

According to an embodiment of the present disclosure, the unit containing at least one carboxyl group includes itaconic acid.

According to an embodiment of the present disclosure, the peptide chains include an oligopeptide, a polypeptide, a protein or a combination thereof.

According to an embodiment of the present disclosure, the oligopeptide includes a fragment CS-1 of fibronectin (FN) or a fragment of vitronectin (VN).

According to an embodiment of the present disclosure, the protein includes the fibronectin (FN) or the vitronectin (VN).

According to an embodiment of the present disclosure, the cross linking reaction is performed by using glutaraldehyde to cross link the polyvinyl alcohol units of the hydrophilic copolymer layer in a sulfuric acid aqueous solution.

According to an embodiment of the present disclosure, performing the cross linking reaction further includes controlling the cross linking reaction time so as to regulate the elastic coefficient of the hydrophilic copolymer layer.

According to an embodiment of the present disclosure, the cross linking reaction time is approximately 0.5 h to 48 h.

According to an embodiment of the present disclosure, the elastic coefficient is in a range of 1 kPa to 100 kPa.

A further aspect of the present disclosure provides a method for culturing undifferentiated stem cells. This culturing method includes: providing a cell culturing article, wherein the cell culturing article includes a substrate, a hydrophilic copolymer layer positioned on the substrate, and a plurality of peptide chains individually conjugated on the hydrophilic copolymer layer. The hydrophilic copolymer layer is copolymerized by a plurality of polyvinyl alcohol units, a plurality of polyvinyl alcohol derivative units, and a plurality of units containing at least one carboxyl group, through a copolymerization reaction. A plurality of undifferentiated stem cells are cultured on the cell culturing article and in a cell culturing medium having definite chemical composition, wherein the undifferentiated stem cells are conjugated to the peptide chains on the cell culturing article. The undifferentiated stem cells are cultured in the cell culturing medium having definite chemical composition continuously for at least five passages.

According to an embodiment of the present disclosure, the stem cells include human adult stem cells, human follicle stem cells (hFSCs), human embryonic stem cells (hESCs) and human induced pluripotent stem cells (hiPSCs).

According to an embodiment of the present disclosure, the peptide chain includes a CS-1 fragment of fibronectin (FN) or a fragment of vitronectin (VN).

According to an embodiment of the present disclosure, in the hydrophilic copolymer layer, the content percentage of the polyvinyl alcohol unit, the polyvinyl alcohol derivative unit and the unit containing at least one carboxyl group are individually about 65-98.7%, 0-30% and 1.3-5%.

According to an embodiment of the present disclosure, the cell culturing medium having definite chemical composition further includes a cell growth factor and a transforming growth factor.

According to an embodiment of the present disclosure, the undifferentiated stem cells are cultured in the cell culturing medium having definite chemical composition for at least ten passages.

Still a further aspect of the present disclosure provides a method for regulating stem cell differentiation. This regulating method includes: providing a cell culturing article, wherein the cell culturing article includes a substrate, a hydrophilic copolymer layer positioned on the substrate, and a plurality of peptide chains individually conjugated on the hydrophilic copolymer layer. The hydrophilic copolymer layer is copolymerized by a plurality of polyvinyl alcohol units, a plurality of polyvinyl alcohol derivative units, and a plurality of units containing at least one carboxyl group, through a copolymerization reaction. The cross linking reaction time of the hydrophilic copolymer layer is regulated such that the hydrophilic copolymer layer has a specific elastic coefficient. The plurality of undifferentiated stem cells are cultured on the cell culturing article and in a cell culturing medium having definite chemical composition, wherein the undifferentiated stem cells are conjugated to the peptide chains on the cell culturing article. The hydrophilic copolymer layer with a specific range of elastic coefficient is utilized to induce differentiation of the undifferentiated stem cells, such that the undifferentiated stem cells are differentiated to desired cell lines.

According to an embodiment of the present disclosure, the integrin includes $\alpha6\beta1$ integrin, $\alpha V\beta3$ integrin, $\alpha V\beta5$ integrin and a combination thereof.

According to an embodiment of the present disclosure, the stem cells include human adult stem cells, human follicle stem cells (hFSCs), human embryonic stem cells (hESCs) and human induced pluripotent stem cells (hiPSCs).

According to an embodiment of the present disclosure, the peptide chain includes the CS-1 fragment of fibronectin (FN) or a fragment of vitronectin (VN).

According to an embodiment of the present disclosure, the cell culturing medium having definite chemical composition further includes a cell growth factor and a transforming growth factor.

According to an embodiment of the present disclosure, the elastic coefficient is in a range of 1 kPa to 100 kPa.

According to an embodiment of the present disclosure, the desired cell lines include neural cells, muscle cells or osteoblast.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

The embodiments of the transparent conductive structure and a method for manufacturing the same of the present disclosure are discussed in detail below, but not limited the scope of the present disclosure. The same symbols or numbers are used to the same or similar portion in the drawings or the description. And the applications of the present disclosure are not limited by the following embodiments and examples which the person in the art can apply in the related field.

The singular forms "a," "an" and "the" used herein include plural referents unless the context clearly dictates otherwise. Therefore, reference to, for example, a metal layer includes embodiments having two or more such metal layers, unless the context clearly indicates otherwise. Reference throughout this specification to "one embodiment" means that a particular feature, structure, or characteristic described in connection with the embodiment is included in at least one embodiment of the present disclosure. Therefore, the appearances of the phrases "in one embodiment" or "in an embodiment" in various places throughout this specification are not necessarily all referring to the same embodiment. Further, the particular features, structures, or characteristics may be combined in any suitable manner in one or more embodiments. It should be appreciated that the following figures are not drawn to scale; rather, the figures are intended; rather, these figures are intended for illustration.

Figure 1A:
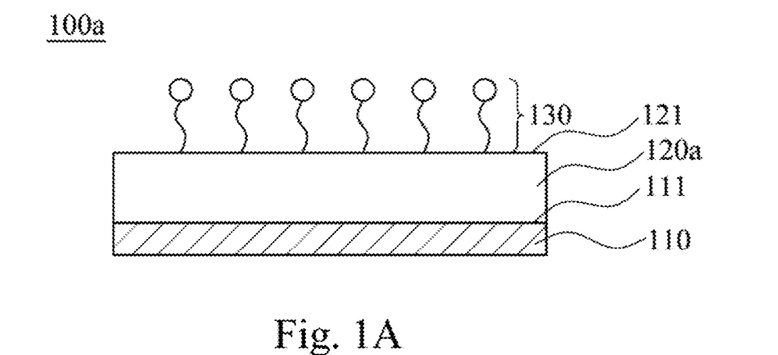
FIGS. 1A-1C are cross-sectional views of cell culturing articles 100a-100c illustrated according to embodiments of the present disclosure.
Figure 1B:
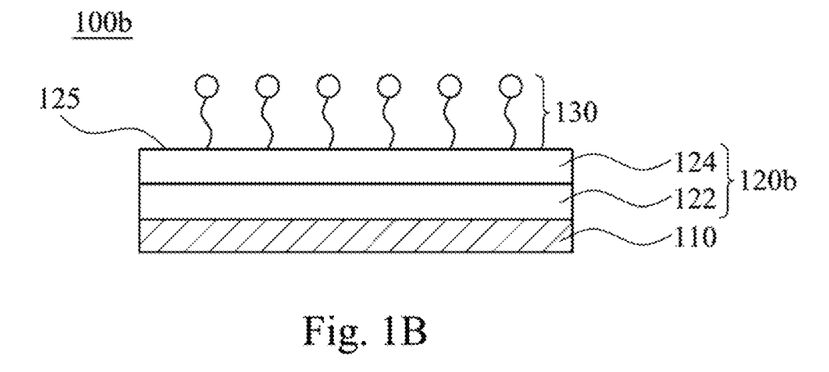
Figure 1C:
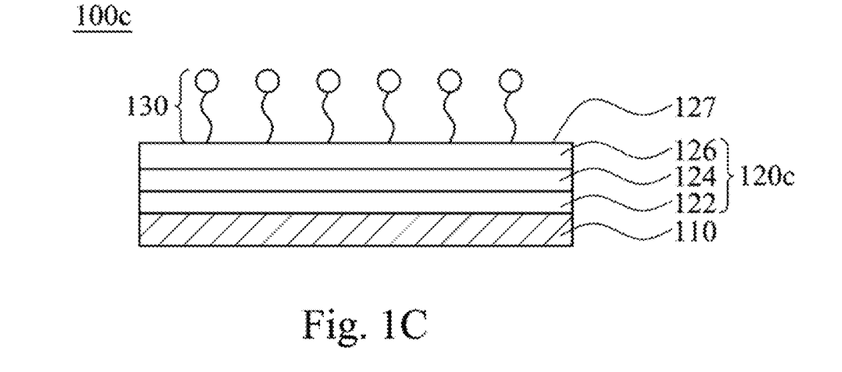

FIGS. 1A-1C are cross-sectional views of cell culturing articles 100a-100c illustrated according to embodiments of the present disclosure.

In FIG. 1A, the cell culturing article 100a includes a substrate 110, a hydrophilic copolymer layer 120a and a peptide chain 130. The substrate 110 has a surface 111, and the hydrophilic copolymer layer 120a is positioned on the surface 111 of the substrate 110. The hydrophilic copolymer layer 120a is copolymerized by polyvinyl alcohol units, polyvinyl alcohol derivative units and units containing at least one carboxyl group. The peptide chains 130 are individually conjugated on a surface 121 of the hydrophilic copolymer layer 120a.

In an embodiment of the present disclosure, the polyvinyl alcohol derivative units include polyvinyl acetate, polyvinyl methyl ether or polyvinyl ethyl ether; and the unit containing at least one carboxyl group includes itaconic acid.

In an embodiment of the present disclosure, the material of the hydrophilic copolymer layer 120a has a chemical formula, i.e., the chemical formula 1 shown below:

wherein, R is a methyl group, ethyl group or acetyl group; x, y and z individually represent content of a polyvinyl alcohol unit, a polyvinyl alcohol derivative unit and a unit containing at least one carboxyl group.

In an embodiment of the present disclosure, in the hydrophilic copolymer layer 120a, the content percentage of the polyvinyl alcohol unit, the polyvinyl alcohol derivative unit and the unit containing at least one carboxyl group are individually about 65-98.7%, 0-30% and 1.3-5%. In an embodiment of the present disclosure, in the hydrophilic copolymer layer 120a, the content percentage of the polyvinyl alcohol unit, the polyvinyl alcohol derivative unit and the unit containing at least one carboxyl group are individually about 85%, 10% and 5%.

In an embodiment of the present disclosure, the hydrophilic copolymer layer 120a has an elastic coefficient. The elastic coefficient is in a range of 1 kPa to 100 kPa.

The peptide chains 130 are individually conjugated on the surface 121 of the hydrophilic copolymer layer 120a. Since the peptide chain 130 is composed of amino acids and has many amino groups, the amino groups of the peptide chain 130 can react with the carboxyl groups of the unit containing at least one carboxyl group to form amide bonds. The peptide chains 130 include an oligopeptide, a polypeptide, a protein or a combination thereof. The oligopeptide includes the CS-1 fragment of fibronectin (FN) or a fragment of vitronectin (VN). The protein includes the fibronectin (FN) or the vitronectin (VN).

The cell culturing article 100b shown in FIG. 1B is similar to the cell culturing article 100a shown in FIG. 1A. In FIG. 1B, the cell culturing article 100b includes a substrate 110, a hydrophilic copolymer layer 120b and a peptide chain 130. The substrate 110 has a surface 111, and the hydrophilic copolymer layer 120b is positioned on the surface 111 of the substrate 110. The hydrophilic copolymer layer 120b is copolymerized by polyvinyl alcohol units, polyvinyl alcohol derivative units and units containing at least one carboxyl group. The peptide chains 130 are individually conjugated on the surface 125 of the hydrophilic copolymer layer 120b.

In an embodiment of the present disclosure, the polyvinyl alcohol derivative units include polyvinyl acetate, polyvinyl methyl ether or polyvinyl ethyl ether; and the unit containing at least one carboxyl group includes itaconic acid.

In an embodiment of the present disclosure, the material of the hydrophilic copolymer layer 120b has a chemical formula, i.e., the chemical formula 1 shown below:

wherein, R is a methyl group, ethyl group or acetyl group; x, y and z individually represent content of a polyvinyl alcohol unit, a polyvinyl alcohol derivative unit and a unit containing at least one carboxyl group.

In an embodiment of the present disclosure, in the hydrophilic copolymer layer 120c, the content percentage of the polyvinyl alcohol unit, the polyvinyl alcohol derivative unit and the unit containing at least one carboxyl group are individually about 65-98.7%, 0-30% and 1.3-5%. In an embodiment of the present disclosure, in the hydrophilic copolymer layer 120c, the content percentage of the polyvinyl alcohol unit, the polyvinyl alcohol derivative unit and the unit containing at least one carboxyl group are individually about 85%, 10% and 5%.

FIG. 1C is different from FIG. 1B in that the hydrophilic copolymer layer 120c of FIG. 1C is composed of a first elastic layer 122, a second elastic layer 124 and a third elastic layer 126. The first elastic layer 122, the second elastic layer 124 and the third elastic layer 126 are copolymerized by the polyvinyl alcohol units, the polyvinyl alcohol derivative units and the units containing at least one carboxyl group, and the difference is only that the elastic coefficients of the first elastic layer 122, the second elastic layer 124 and the third elastic layer 126 are different. Since the first elastic layer 122, the second elastic layer 124 and the third elastic layer 126 have different elastic coefficients, the elastic coefficient of the hydrophilic copolymer layer 120c can be controlled thereby. In an embodiment of the present disclosure, the elastic coefficient of the hydrophilic copolymer layer 120c is in a range of 1 kPa to 100 kPa.

The peptide chains 130 are individually conjugated on the surface 127 of the hydrophilic copolymer layer 120c. Since the peptide chain 130 is composed of amino acids and has many amino groups, the amino groups of the peptide chain 130 can react with the carboxyl groups of the unit containing at least one carboxyl group to form amide bonds. The peptide chain 130 includes oligopeptide, polypeptide, protein or a combination thereof. The oligopeptide includes the CS-1 fragment of fibronectin (FN) or a fragment of vitronectin (VN). The protein includes the fibronectin (FN) or the vitronectin (VN).

Figure 2A:
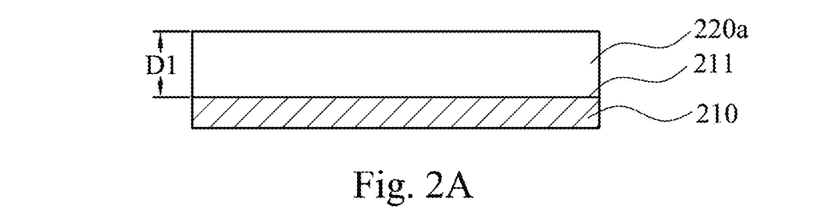
FIGS. 2A-2C are cross-sectional views of stages for manufacturing the cell culturing article illustrated according to embodiments of the present disclosure.
Figure 2B:
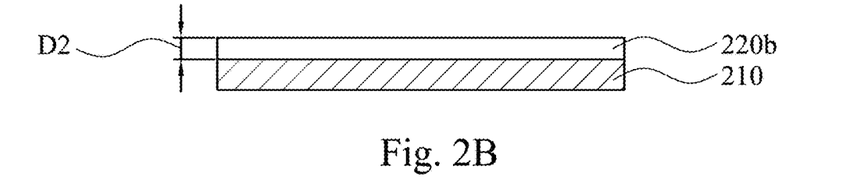
Figure 2C:
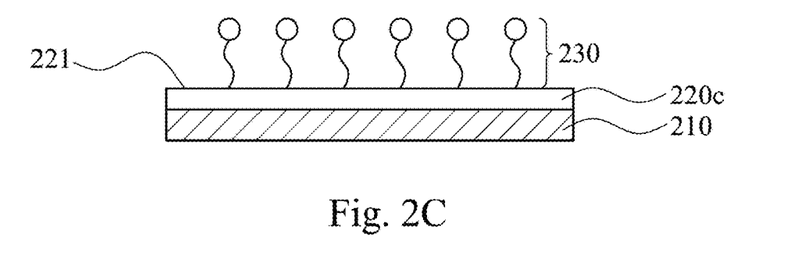

FIGS. 2A-2C are cross-sectional views of stages for manufacturing the cell culturing article illustrated according to embodiments of the present disclosure.

In FIG. 2A, a substrate 210 having a surface 211 is provided, and a hydrophilic copolymer layer 220a is formed on the surface 211 of the substrate 210. The hydrophilic copolymer layer 220a is copolymerized by a plurality of polyvinyl alcohol units, a plurality of polyvinyl alcohol derivative units, and a plurality of units containing at least one carboxyl group, through a copolymerization reaction. In an embodiment of the present disclosure, the polyvinyl alcohol derivative units include polyvinyl acetate, polyvinyl methyl ether or polyvinyl ethyl ether; and the unit containing at least one carboxyl group includes itaconic acid.

In an embodiment of the present disclosure, the method further includes first preparing a hydrophilic copolymer solution, and then coating the hydrophilic copolymer solution onto the surface 211 of the substrate 210 to form a hydrophilic copolymer layer 220a. The hydrophilic copolymer solution includes a hydrophilic copolymer with the concentration of about 0.05-0.2 wt %. In FIG. 2A, the hydrophilic copolymer layer 220a has a thickness (D1) that is larger than 9 micrometers.

In FIG. 2B, a cross linking reaction is performed such that the polyvinyl alcohol units of the hydrophilic copolymer layer 220a of FIG. 2A are cross-linked with each other to form a hydrophilic copolymer layer 220b. In an embodiment of the present disclosure, glutaraldehyde is utilized to cross link the polyvinyl alcohol units of the hydrophilic copolymer layer in a sulfuric acid aqueous solution. By performing the cross linking reaction and controlling the cross linking reaction time, the elastic coefficient of the hydrophilic copolymer layer 220b is regulated. In an embodiment of the present disclosure, the cross linking reaction time is about 0.5 h to 48 h, and the elastic coefficient of the hydrophilic copolymer layer 220b is in a range of 1 kPa to 100 kPa. In an embodiment of the present disclosure, the hydrophilic copolymer layer 200b has a thickness (D2) in a range of about 2.0-9.0 micrometers.

Figure 3:
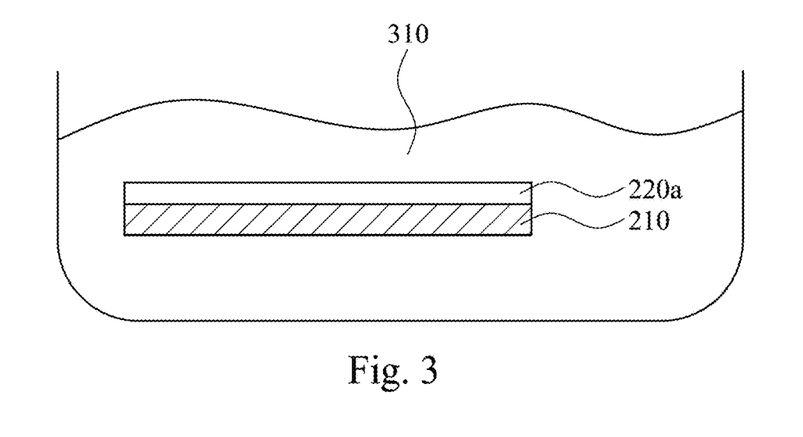
FIG. 3 is a schematic view of a cross linking step illustrated according to an embodiment of the present disclosure.

In the cross linking reaction, the structure of FIG. 2A is immersed in a cross linking reaction solution 310, such that the hydrophilic copolymer layer 220a of FIG. 2A is reacted to form the hydrophilic copolymer layer 220b, as shown in FIG. 3. In an embodiment of the present disclosure, the cross linking reaction solution 310 includes glutaraldehyde of 0.1 wt %, sulphuric acid ($H_2SO_4$) of 1.0 wt % and sodium sulfate ($Na_2SO_4$) of 20.0 wt %. The cross linking reaction is as shown in the reaction scheme 1 below:

In the reaction scheme 1, under the action of sulphuric acid, the polyvinyl alcohol units of the hydrophilic copolymer is reacted with the glutaraldehyde to form a cross-linked hydrophilic copolymer having an acetal group. When the cross linking reaction time is longer, the cross linking degree of the hydrophilic copolymer layer is higher, and the elastic coefficient of the hydrophilic copolymer layer is also increased accordingly. As shown in table 1, when the cross linking reaction time is longer, the water content of the hydrophilic copolymer layer is lower. If the hydrophilic copolymer layer is dried and then immersed, when the cross linking reaction time is longer, the thickness difference throughout the hydrophilic copolymer layer is less.

TABLE 1

| | Cross Linking Reaction Time (hour) | elastic coefficient (kPa) | Water Content (%) | Thickness of Dried Layer (micrometer) | Thickness of Immersed Layer (micrometer) |
|---|---|---|---|---|---|
| Embodiment 1* | 0.5 | 3.7 | 83.2 | 1.5 | 8.9 |
| Embodiment 2* | 1 | 10.3 | 70.7 | 1.5 | 5.1 |
| Embodiment 3* | 6 | 12.2 | 58.5 | 1.5 | 3.6 |
| Embodiment 4* | 24 | 25.3 | 36.1 | 1.5 | 2.3 |
| Embodiment 5* | 48 | 30.4 | 31.4 | 1.5 | 2.2 |

*the material of embodiments 1-5 is the hydrophilic copolymer copolymerized by polyvinyl alcohol units, polyvinyl alcohol derivative units and units containing at least one carboxyl group.

In FIG. 2C, the peptide chains 230 are individually conjugated on the surface 221 of the hydrophilic copolymer layer 220c. The peptide chain 230 is polymerized by amino acids, wherein one end of the skeleton of the peptide chain 230 contain an amino group (—NH2), and some of the amino acids contain an amino (—NH2) side chain. When the peptide chain 230 is presented with a primary structure, the amino group of the peptide chain 230 reacts with the carboxyl group of the hydrophilic copolymer layer 220c to form an amide bond. The amino group of the peptide chain 230 may be one end of the peptide chain 230, or a side chain of the amino acid. Additionally, the peptide chains 230 are individually conjugated on the surface 221 of the hydrophilic copolymer layer 220c.

When the peptide chain 230 is presented with a structure higher than the secondary structure, some amino groups of the peptide chain 230 may be exposed on the surface of the structure of the peptide chain 230. These amino groups exposed on the surface of the peptide chain 230 react with the carboxyl groups of the hydrophilic copolymer layer 220c to form amide bonds. The amino group of the peptide chain 230 may be one end of the peptide chain 230, or a side chain of the amino acid. Additionally, the peptide chains 230 are individually conjugated on the surface 221 of the hydrophilic copolymer layer 220c.

In an embodiment of the present disclosure, the peptide chains 230 include an oligopeptide, a polypeptide, a protein or a combination thereof. The oligopeptide includes a CS-1 fragment of fibronectin (FN) or a fragment of vitronectin (VN). The protein includes the fibronectin (FN) or the vitronectin (VN).

The step of individually conjugating the peptide chains onto the surface of the hydrophilic copolymer layer is as shown in the reaction scheme 2 below:

In the reaction scheme 2, the surface of the hydrophilic copolymer layer is shown as containing only one carboxyl group for purpose of simplification and illustration. However, in an actual structure of the hydrophilic copolymer layer, the surface of the hydrophilic copolymer layer contains a plurality of carboxyl groups, and all of the carboxyl groups can react as shown in the reaction scheme 2 to individually conjugate the plurality of peptide chains onto the surface of the hydrophilic copolymer layer. The amino groups of the peptide chain react with the carboxyl groups of the hydrophilic copolymer layer to form amide bonds. The amino group of the peptide chain may be one end of the peptide chain, or a side chain of the amino acid. The peptide chains are individually conjugated on the surface of the hydrophilic copolymer layer.

Figure 4:
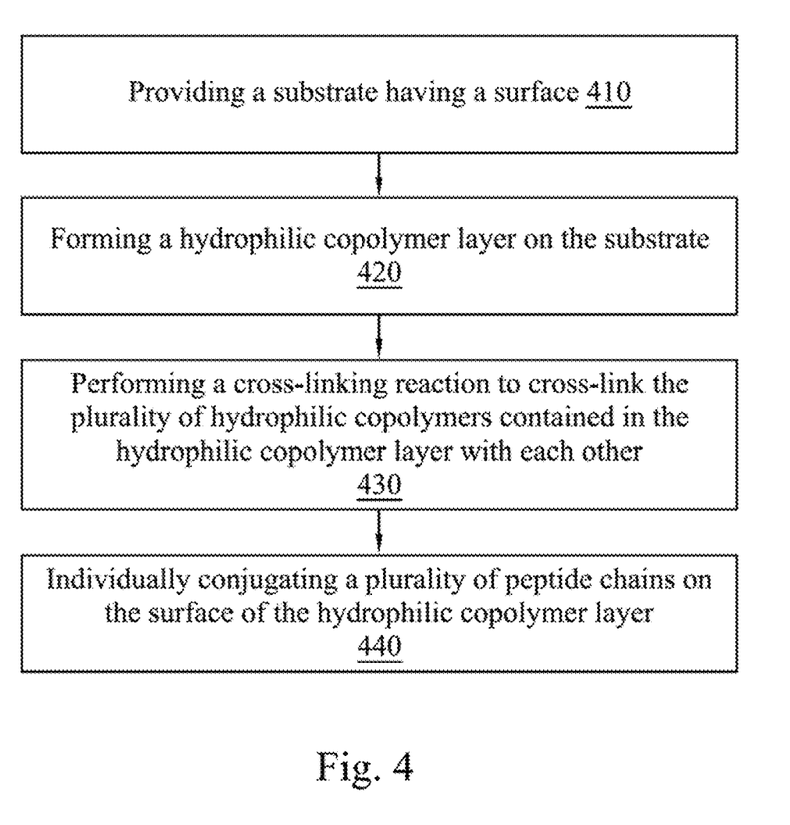
FIG. 4 is a flowchart of stages for manufacturing the cell culturing article illustrated according to embodiments of the present disclosure.

FIG. 4 is a flowchart of stages for manufacturing the cell culturing article illustrated according to embodiments of the present disclosure. The steps 410-440 of FIG. 4 are used together with FIG. 2, i.e. the cross-sectional view of stages of manufacturing a cell culturing article, to disclose stages of manufacturing the cell culturing article.

In step 410, a substrate 210 having a surface 211 is provided. Then the hydrophilic copolymer layer 220a is formed on the surface 211 of the substrate 210, wherein the hydrophilic copolymer layer 220a is copolymerized by a plurality of polyvinyl alcohol units, a plurality of polyvinyl alcohol derivative units and a plurality of units containing at least one carboxyl group, through a copolymerization reaction, as illustrated in step 420. In an embodiment of the present disclosure, the polyvinyl alcohol derivative units include polyvinyl acetate, polyvinyl methyl ether or polyvinyl ethyl ether; and the unit containing at least one carboxyl group includes itaconic acid. As shown in FIG. 2(a), the hydrophilic copolymer layer 220a has a thickness (D1) that is larger than 9 micrometers.

In an embodiment of the present disclosure, the method further includes first preparing a hydrophilic copolymer solution, and then coating the hydrophilic copolymer solution onto the surface of the substrate to form a hydrophilic copolymer layer 220a. The hydrophilic copolymer solution includes a hydrophilic copolymer with the concentration of about 0.05-0.2 wt %.

In step 430, a cross linking reaction is performed such that the polyvinyl alcohol units of the hydrophilic copolymer layer 220a are cross-linked with each other to form a hydrophilic copolymer layer 220b. In an embodiment of the present disclosure, glutaraldehyde is utilized to cross link the polyvinyl alcohol units of the hydrophilic copolymer in a sulfuric acid aqueous solution. By performing the cross linking reaction and controlling the cross linking reaction time, the elastic coefficient of the hydrophilic copolymer layer 200b is regulated. In an embodiment of the present disclosure, the cross linking reaction time is about 0.5 h to 48 h, and the elastic coefficient of the hydrophilic copolymer layer 200b is in a range of 1 kPa to 100 kPa. As shown in FIG. 2(b), the hydrophilic copolymer layer 200b has a thickness (D2) in a range of about 2.0-9.0 micrometers.

In step 440, the peptide chains 230 are individually conjugated on the surface 221 of the hydrophilic copolymer layer 220c. In an embodiment of the present disclosure, the peptide chains 230 include oligopeptides, polypeptides, proteins or a combination thereof. The oligopeptide includes the CS-1 fragment of fibronectin (FN) or a fragment of vitronectin (VN). The protein includes the fibronectin (FN) or the vitronectin (VN).

Figure 5:
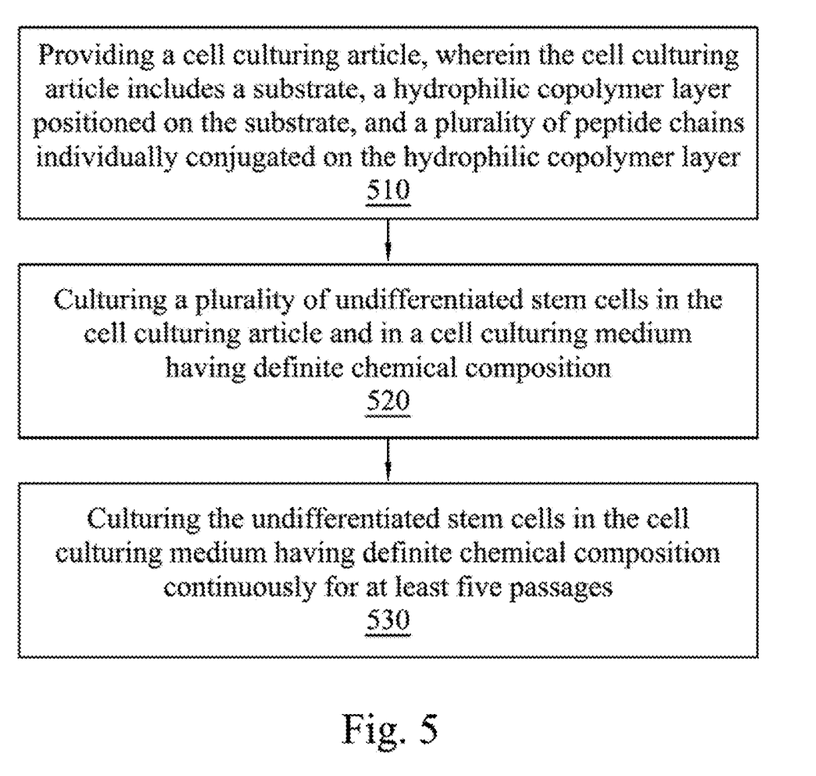
FIG. 5 is a flowchart of stages for culturing undifferentiated stem cells illustrated according to embodiments of the present disclosure.

FIG. 5 is a flowchart of stages for culturing undifferentiated stem cells illustrated according to embodiments of the present disclosure. In FIG. 5 steps 510-530 illustrate stages of culturing cells with the cell culturing article 100a shown in FIG. 1A.

In step 510, the cell culturing article 100a is first provided. The cell culturing article 100a includes a substrate 110, a hydrophilic copolymer layer 120a positioned on the substrate 110, and peptide chains 130 individually conjugated on the hydrophilic copolymer layer 120a. The hydrophilic copolymer layer 120a is copolymerized by the polyvinyl alcohol units, the polyvinyl alcohol derivative units and units containing at least one carboxyl group, through a copolymerization reaction. In an embodiment of the present disclosure, in the hydrophilic copolymer layer 120a, the content percentage of the polyvinyl alcohol unit, the polyvinyl alcohol derivative unit and the unit containing at least one carboxyl group are individually about 65-98.7%, 0-30% and 1.3-5%. In an embodiment of the present disclosure, the peptide chain includes the CS-1 fragment of fibronectin (FN) or a fragment of vitronectin (VN).

In step 520, undifferentiated stem cells are cultured on the cell culturing article 100a and in a cell culturing medium having definite chemical composition, wherein the undifferentiated stem cells are conjugated to the peptide chains 30 on the cell culturing article 100a. In an embodiment of the present disclosure, the stem cells include human adult stem cells, human follicle stem cells (hFSCs), human embryonic stem cells (hESCs) and human induced pluripotent stem cells (hiPSCs). In an embodiment of the present disclosure, the cell culturing medium having definite chemical composition further includes a cell growth factor and a transforming growth factor.

In step 530, the undifferentiated stem cells are cultured in the cell culturing medium having definite chemical composition continuously for at least five passages. In an embodiment of the present disclosure, the undifferentiated stem cells are cultured in the cell culturing medium having definite chemical composition for at least ten passages.

Figure 6:
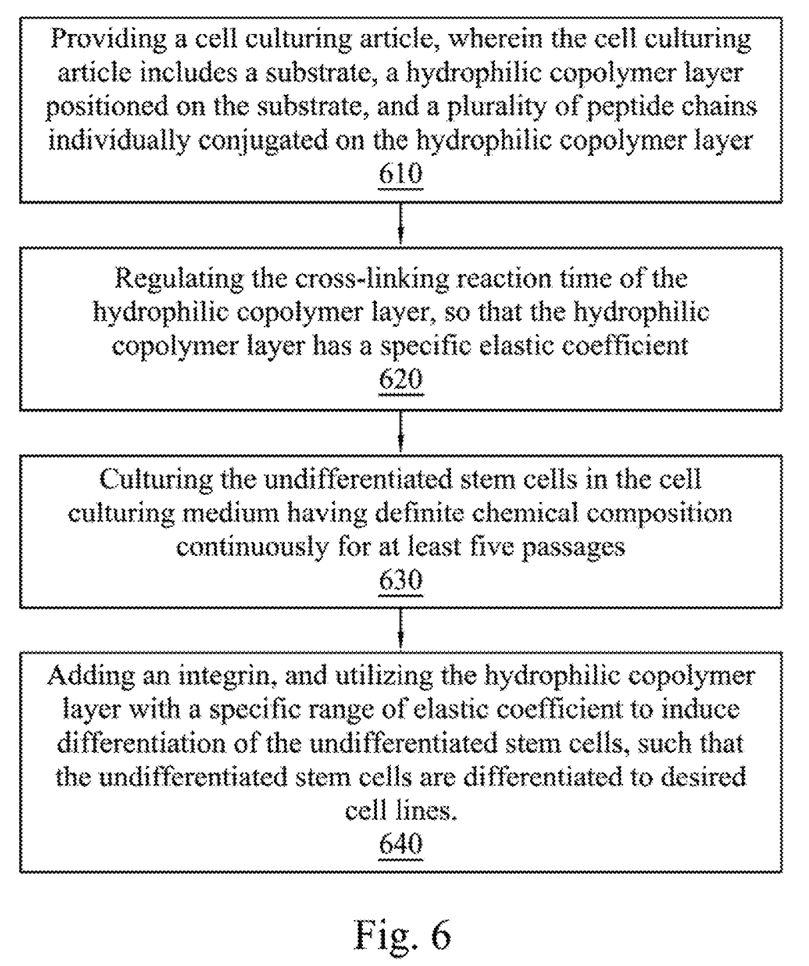
FIG. 6 is a flowchart of stages for regulating stem cell differentiation illustrated according to embodiments of the present disclosure.

FIG. 6 is a flowchart of stages for regulating stem cell differentiation illustrated according to embodiments of the present disclosure. In FIG. 6 steps 610-640 illustrate stages of regulating stem cell differentiation with the cell culturing article 100a shown in FIG. 1A.

In step 610, the cell culturing article 100a is provided. The cell culturing article 100a includes a substrate 110, a hydrophilic copolymer layer 120a positioned on the substrate 110, and peptide chains 130 individually conjugated on the hydrophilic copolymer layer 120a. The hydrophilic copolymer layer 120a is copolymerized by the polyvinyl alcohol units, the polyvinyl alcohol derivative units and units containing at least one carboxyl group, through a copolymerization reaction. In an embodiment of the present disclosure, in the hydrophilic copolymer layer 120a, the content percentage of the polyvinyl alcohol unit, the polyvinyl alcohol derivative unit and the unit containing at least one carboxyl group are individually about 65-98.7%, 0-30% and 1.3-5%. In an embodiment of the present disclosure, the peptide chain includes the CS-1 fragment of fibronectin (FN) or a fragment of vitronectin (VN).

In step 620, the cross linking reaction time of the hydrophilic copolymer layer 120a is regulated, such that the hydrophilic copolymer layer 120a has a specific elastic coefficient. By controlling the cross linking reaction time, the elastic coefficient of the hydrophilic copolymer layer 120a is regulated. In an embodiment of the present disclosure, the cross linking reaction time is about 0.5 h to 48 h, and the elastic coefficient of the hydrophilic copolymer layer 120a is in a range of 1 kPa to 100 kPa.

In step 630, undifferentiated stem cells are cultured on the cell culturing article 100a and in a cell culturing medium having definite chemical composition, wherein the undifferentiated stem cells are conjugated to the peptide chains 130 on the cell culturing article 100a. In an embodiment of the present disclosure, the stem cells include human adult stem cells, human follicle stem cells (hFSCs), human embryonic stem cells (hESCs) and human induced pluripotent stem cells (hiPSCs).

In step 640, an integrin is added, and the hydrophilic copolymer layer 120a with a specific range of elastic coefficient is utilized to induce differentiation of the undifferentiated stem cells, such that the undifferentiated stem cells are differentiated to desired cell lines. In an embodiment of the present disclosure, the cell culturing medium having definite chemical composition further includes a cell growth factor and a transforming growth factor. In an embodiment of the present disclosure, the desired cell lines include neural cells, muscle cells or osteoblast.

In an embodiment of the present disclosure, when the elastic coefficient of the hydrophilic copolymer layer is about 1 kPa, the undifferentiated stem cells are induced to be differentiated to neural cells. when the elastic coefficient of the hydrophilic copolymer layer is about 10 kPa, the undifferentiated stem cells are induced to be differentiated to muscle cells. when the elastic coefficient of the hydrophilic copolymer layer is about 100 kPa, the undifferentiated stem cells are induced to be differentiated to osteoblast.

In an embodiment of the present disclosure, by controlling the cross linking reaction time, the elastic coefficient of the hydrophilic copolymer layer is regulated. Table 2 shows the elastic coefficients of embodiments 1-5 and a comparative example 1.

TABLE 2

|  | cross linking reaction time (hour) | elastic coefficient (kPa) |
|---|---|---|
| Embodiment 1* | 0.5 | 3.7 |
| Embodiment 2* | 1 | 10.3 |
| Embodiment 3* | 6 | 12.2 |
| Embodiment 4* | 24 | 25.3 |
| Embodiment 5* | 48 | 30.4 |
| Comparative Example 1** | — | 1,200 |

*the material of embodiments 1-5 is the hydrophilic copolymer copolymerized by polyvinyl alcohol units, polyvinyl alcohol derivative units and units containing at least one carboxyl group.
**the material of the comparative example 1 is tissue culture polystyrene (TCPS).

It can be seen from table 2 that when the cross linking reaction time is longer, the elastic coefficient of the hydrophilic copolymer layer is higher. The cross linking reaction time of embodiment 1 is 0.5 h, and the resultant elastic coefficient of the hydrophilic copolymer layer is the lowest (11.1). Additionally, the cross linking reaction time of embodiment 5 is 48 h, and the resultant elastic coefficient of the hydrophilic copolymer layer is the highest (91.2). Compared with the hydrophobic material (i.e., TCPS) of the comparative example 1, in embodiments 1-5 of the present disclosure the elastic coefficient of the hydrophilic copolymer layer can be regulated by controlling the drying time.

Additionally, when the cross linking reaction time of the hydrophilic copolymer layer is longer, the elastic coefficient is higher, and the differentiation ratio of the stem cells cultured on the hydrophilic copolymer layer is accordingly increased, with reference to table 3. Table 3 shows the stem cell differentiation ratio of embodiments 6-11 and a comparative example 2.

TABLE 3

| | cross linking reaction time (hour) | stem cell differentiation ratio (%) |
|---|---|---|
| Embodiment 6* | 1 | not provided |
| Embodiment 7* | 4 | 2 |
| Embodiment 8* | 6 | 5 |
| Embodiment 9* | 12 | 10 |
| Embodiment 10* | 24 | 15 |
| Embodiment 11* | 48 | 60 |
| Comparative Example 2** | — | 25 |

*the material of embodiments 6-11 is the hydrophilic copolymer copolymerized by polyvinyl alcohol units, polyvinyl alcohol derivative units and units containing at least one carboxyl group.
**the material of the comparative example is Corning Synthemax.

It can be seen from table 3 that when the cross linking reaction time of the hydrophilic copolymer layer is longer, the elastic coefficient of the hydrophilic copolymer layer is higher, and the differentiation ratio of the stem cells cultured on the hydrophilic copolymer layer is accordingly larger. The cross linking reaction time of the embodiment 6 is 1 h, so that the resultant stem cell differentiation ratio is the lowest. Moreover, the cross linking reaction time of the embodiment 11 is 48 h, so that the resultant stem cell differentiation ratio is the highest. Compared with the comparative example 2, in the embodiments of the present disclosure by controlling the cross linking reaction time, the elastic coefficient of the hydrophilic copolymer layer is regulated, and the differentiation efficiency of stem cells is significantly improved.

Figure 7A:
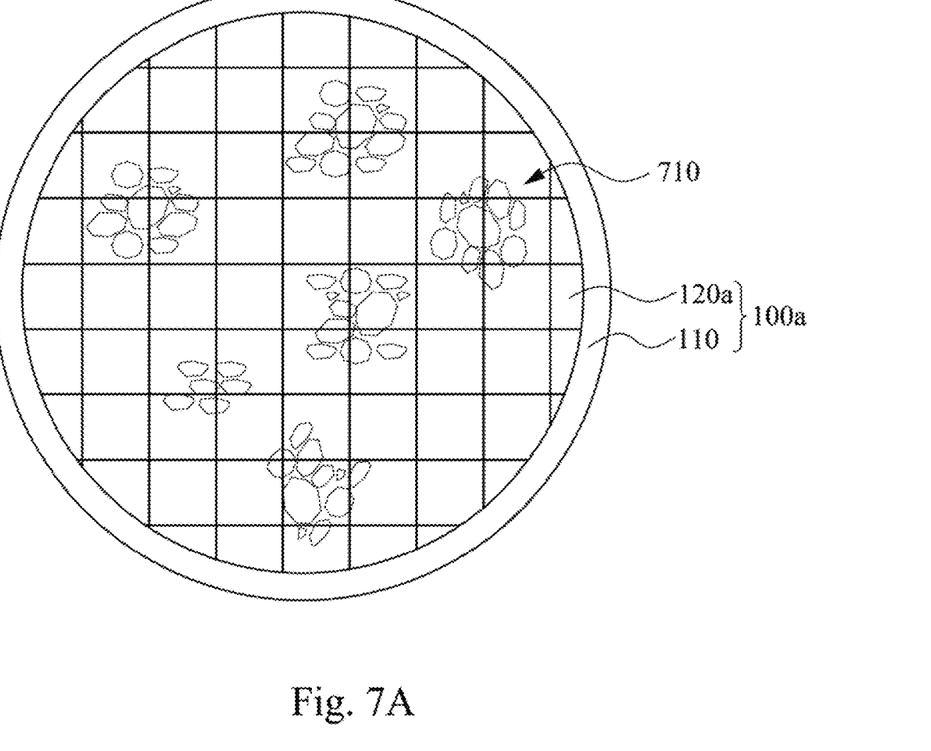
FIG. 7A is a top view of culturing cells with the cell culturing article 110 illustrated according to embodiments of the present disclosure.

FIG. 7A is a top view of culturing cells with the cell culturing article 100a of FIG. 1A. The cell culturing article includes a substrate 110 and a hydrophilic copolymer layer 120a, and a plurality of cell clusters 710 are cultured on the hydrophilic copolymer layer 120. In an embodiment of the present disclosure, the cell clusters 710 include human adult stem cells, human follicle stem cells (hFSCs), human embryonic stem cells (hESCs) and human induced pluripotent stem cells (hiPSCs).

In an embodiment of the present disclosure, the hydrophilic copolymer layer 120a is copolymerized by the polyvinyl alcohol units, the polyvinyl alcohol derivative units and the units containing at least one carboxyl group, through a copolymerization reaction. The polyvinyl alcohol derivative units include polyvinyl acetate, polyvinyl methyl ether or polyvinyl ethyl ether; and the unit containing at least one carboxyl group includes itaconic acid.

Figure 7B:
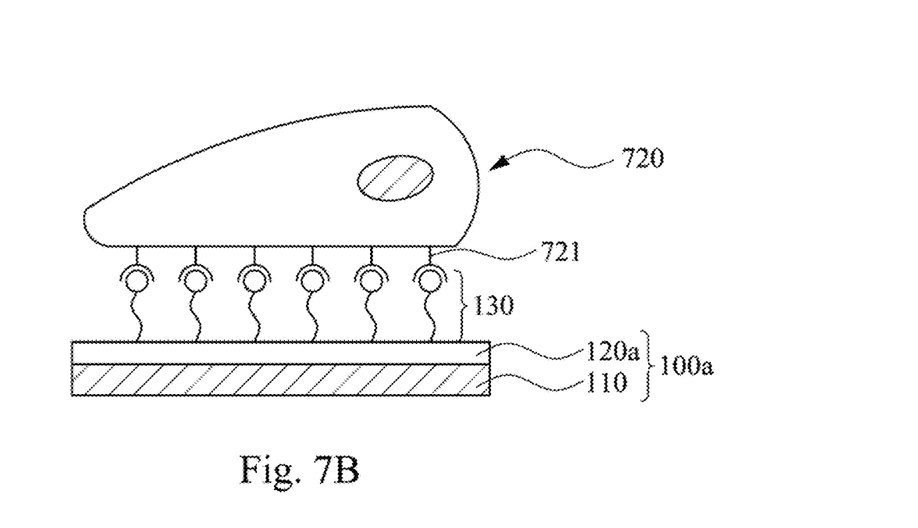
FIG. 7B is a cross-sectional view of culturing cells with the cell culturing article 110 illustrated according to embodiments of the present disclosure.

FIG. 7B is a cross-sectional view of culturing cells with the cell culturing article 100a of FIG. 1A. In FIG. 7B, the cell culturing article 100a includes a substrate 110, a hydrophilic copolymer layer 120a and a peptide chain 130. The hydrophilic copolymer layer 120a is positioned on the substrate 110, and the peptide chains 130 are individually conjugated on the surface of the hydrophilic copolymer layer 120a.

Cells 720 are cultured on the hydrophilic copolymer layer 120a. The cells 720 have many receptors 721, wherein the receptor 721 can be fixed on the surface of the hydrophilic copolymer layer 120a by conjugating with the peptide chains 130 on the surface of the hydrophilic copolymer layer 120a through a specific interaction force.

In an embodiment of the present disclosure, the cells 720 include human adult stem cells, human follicle stem cells (hFSCs), human embryonic stem cells (hESCs) and human induced pluripotent stem cells (hiPSCs). In an embodiment of the present disclosure, the peptide chains 130 include oligopeptides, polypeptides, proteins or a combination thereof. The oligopeptide includes the CS-1 fragment of fibronectin (FN) or a fragment of vitronectin (VN). The protein includes the fibronectin (FN) or the vitronectin (VN).

In an embodiment of the present disclosure, the hydrophilic copolymer layer 120a is copolymerized by the polyvinyl alcohol units, the polyvinyl alcohol derivative units and the units containing at least one carboxyl group, through a copolymerization reaction. The polyvinyl alcohol derivative units include polyvinyl acetate, polyvinyl methyl ether or polyvinyl ethyl ether; and the unit containing at least one carboxyl group includes itaconic acid.

Figure 8A:
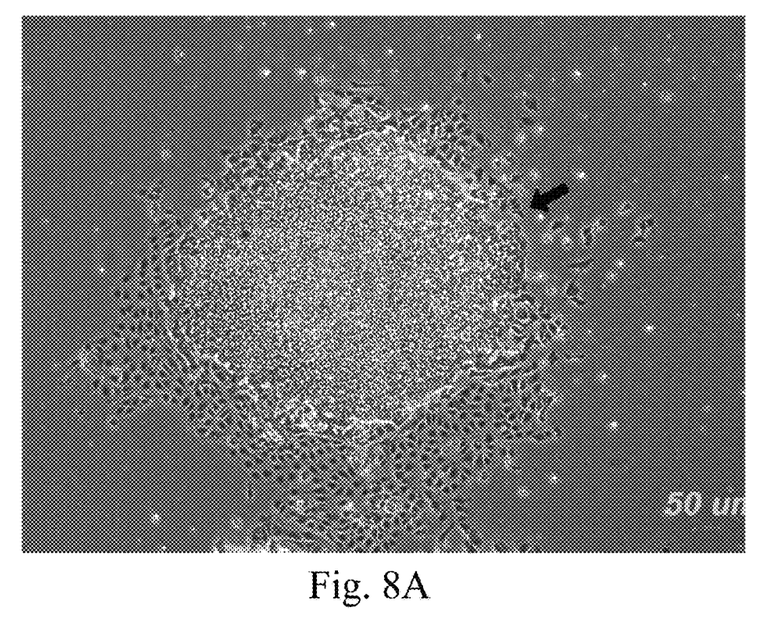
FIG. 8A is an image of culturing cells with a general cell culturing article.

FIG. 8A is an image of culturing cells with the cell culturing article of the comparative example 2, wherein the cell culturing article of the comparative example 2 is purchased from Corning with the model number of Corning Synthemax. In FIG. 8A, when cells are cultured with the cell culturing article of the comparative example 2, the density of the cell clusters (as indicated by the arrow) is loose.

Figure 8B:
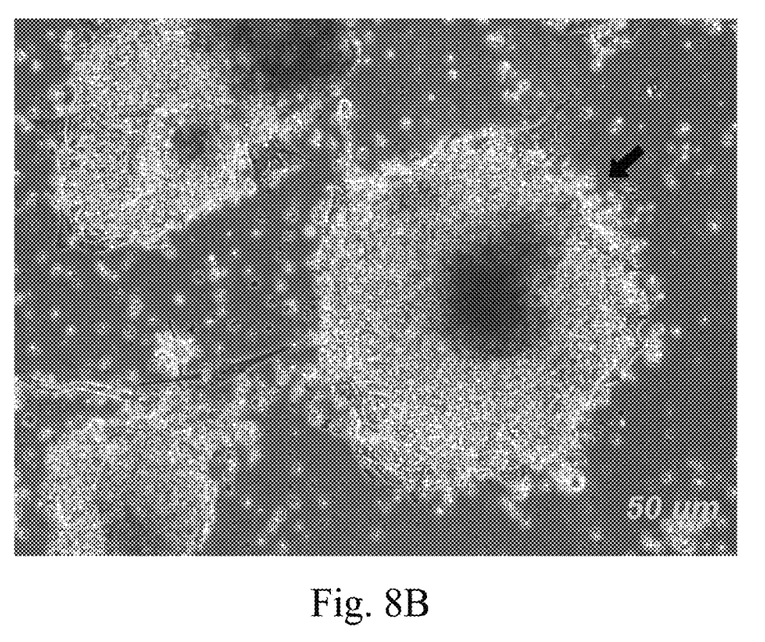
FIG. 8B is an image of culturing cells with the cell culturing article provided in the embodiments of the present disclosure.

FIG. 8B is an image of culturing cells with the cell culturing article of the embodiment 7, wherein the cross linking reaction time of the hydrophilic copolymer layer of the embodiment 7 is 4 h. As compared with FIG. 8A, when cells are cultured with the cell culturing article of the embodiment 7, the density of the cell clusters (as indicated by the arrow) is relative compact.

In an embodiment of the present disclosure, the cell culturing article is conjugated with a receptor on the surface of a cell to be cultured through the peptide chain conjugated on the hydrophilic copolymer layer, such that the cell can adhere onto the surface of the hydrophilic copolymer layer, rather than liable to suspending in a cell culture medium, which otherwise will lead to death of the cells being cultured. As the cells are not liable to suspend in the cell culture medium due to the better hydrophilic nature of the hydrophilic copolymer layer, the cell viability of the cells being cultured is increased.

Additionally, in a natural environment, since a certain range of elastic stress exists between the undifferentiated stem cell and the tissue, the elastic stress can induce the undifferentiated stem cell to be differentiated to a specific cell. The cell culturing article provided in the embodiments of the present disclosure can induce the stem cells to be differentiated to a cell of a specific type by regulating the elastic coefficient of the hydrophilic copolymer layer, and thus can increase the differentiation ratio of stem cells.

Although embodiments of the present disclosure and their advantages have been described in detail, they are not used to limit the present disclosure. It should be understood that various changes, substitutions and alterations can be made herein without departing from the spirit and scope of the present disclosure. Therefore, the protecting scope of the present disclosure should be defined as the following claims.

What is claimed is:

1. A cell culturing article, comprising:
   a base layer having a surface;
   a hydrophilic copolymer layer positioned on the base layer, wherein the hydrophilic copolymer layer comprises a plurality of polyvinyl alcohol units, a plurality of polyvinyl alcohol derivative units and a plurality of itaconic acid units, the itaconic acid units comprise a plurality of carboxyl groups; and
   a plurality of peptide chains individually conjugated on a surface of the hydrophilic copolymer layer, and at least one amino group of each of the peptide chains reacting with one of the carboxyl groups of the itaconic acid units to form an amide bond.

2. The cell culturing article of claim 1, wherein the polyvinyl alcohol derivative units comprise polyvinyl acetate, polyvinyl methyl ether or polyvinyl ethyl ether.

3. The cell culturing article of claim 1, in the hydrophilic copolymer layer, wherein the content percentages of the polyvinyl alcohol units, the polyvinyl alcohol derivative units and the units containing at least one carboxyl group are respectively 65-98.7%, 0-30% and 1.3-5%.

4. The cell culturing article of claim 1, in the hydrophilic copolymer layer, wherein the content percentages of the polyvinyl alcohol units, the polyvinyl alcohol derivative units and the units containing at least one carboxyl group are respectively 85%, 10% and 5%.

5. The cell culturing article of claim 1, wherein the hydrophilic copolymer layer has an elastic coefficient.

6. The cell culturing article of claim 5, wherein the elastic coefficient is in a range of 1 kPa to 100 kPa.

7. The cell culturing article of claim 1, wherein the peptide chains comprises an oligopeptide, a polypeptide, a protein, or a combination thereof.

8. The cell culturing article of claim 7, wherein the oligopeptide comprises a fragment CS-1 of fibronectin (FN) or a fragment of vitronectin (VN).

9. The cell culturing article of claim 7, wherein the protein comprises the fibronectin (FN) or the vitronectin (VN).

* * * * *